United States Patent
Suzuki et al.

(10) Patent No.: US 9,045,398 B2
(45) Date of Patent: Jun. 2, 2015

(54) SULFONIUM SALT AND PHOTO-ACID GENERATOR

(71) Applicants: SAN-APRO LTD., Kyoto-shi, Kyoto (JP); TOKYO OHKA KOGYO CO., LTD., Kawasaki-shi, Kanagawa-ken (JP)

(72) Inventors: Issei Suzuki, Kyoto (JP); Takuya Ikeda, Kyoto (JP); Yusaku Takashima, Kyoto (JP); Takeshi Furuta, Kyoto (JP); Yoshitaka Komuro, Kawasaki (JP); Yoshiyuki Utsumi, Kawasaki (JP); Takaaki Kaiho, Kawasaki (JP); Toshiaki Hato, Kawasaki (JP)

(73) Assignees: SAN-APRO LIMITED, Kyoto-shi (JP); TOKYO OHKA KOGYA CO. LTD., Kawasaki-shi (JP)

( * ) Notice: Subject to any disclaimer, the term of this patent is extended or adjusted under 35 U.S.C. 154(b) by 0 days.

(21) Appl. No.: 14/289,686

(22) Filed: May 29, 2014

(65) Prior Publication Data

US 2014/0357896 A1 Dec. 4, 2014

(30) Foreign Application Priority Data

May 31, 2013 (JP) ................ 2013-114827

(51) Int. Cl.
  C07C 281/12 (2006.01)
  C07C 309/06 (2006.01)
  C07C 309/19 (2006.01)
  C07C 311/48 (2006.01)
  C07C 317/04 (2006.01)
  C07C 381/12 (2006.01)

(52) U.S. Cl.
  CPC ............ *C07C 309/06* (2013.01); *C07C 309/19* (2013.01); *C07C 311/48* (2013.01); *C07C 317/04* (2013.01); *C07C 381/12* (2013.01); *C07C 2102/42* (2013.01)

(58) Field of Classification Search
  CPC .................................................. C07C 381/12
  USPC ......... 430/138, 270.1, 281.1, 302; 568/74, 77
  See application file for complete search history.

(56) References Cited

U.S. PATENT DOCUMENTS

| 2,800,747 | A * | 7/1957 | Pitt ............................. 47/58.1 R |
| 7,442,485 | B2 * | 10/2008 | Oshima et al. ................ 430/138 |
| 7,642,368 | B2 * | 1/2010 | Sumino et al. ................ 558/412 |

FOREIGN PATENT DOCUMENTS

| JP | 2002-193925 A | 7/2002 |
| JP | 2005-91976 A | 4/2005 |
| JP | 2013-33161 A | 2/2013 |
| JP | 2013-47211 A | 3/2013 |
| JP | 2013-80240 A | 5/2013 |
| JP | 2013-80245 A | 5/2013 |
| JP | 2013-92657 A | 5/2013 |
| WO | 02/18332 A1 | 3/2002 |
| WO | 2005/037778 A1 | 4/2005 |

* cited by examiner

*Primary Examiner* — Kamal Saeed
*Assistant Examiner* — Janet L Coppins
(74) *Attorney, Agent, or Firm* — Westerman, Hattori, Daniels & Adrian, LLP

(57) ABSTRACT

Provided is a novel sulfonium salt that has high solubility in a solvent and has high light sensitivity to, especially, light having a wavelength not longer than deep-UV (254 nm) and a novel photo-acid generator comprising the sulfonium salt. The invention relates to a sulfonium salt represented by the following general formula (1) and a novel photo-acid generator comprising the sulfonium salt.

[Chemical Formula 1]

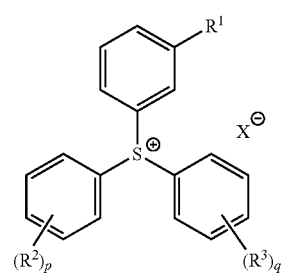

(1)

wherein $R^1$ represents an electron withdrawing group; $R^2$ and $R^3$ each independently represent an alkyl group having 1 to 5 carbon atoms, an alkoxy group, an acyl group, a halogenated alkyl group, a halogen atom, a hydroxyl group, a cyano group, or a nitro group; p and q each independently represent an integer of 0 to 5; and $X^-$ represents a monovalent counter anion.

6 Claims, No Drawings

SULFONIUM SALT AND PHOTO-ACID GENERATOR

TECHNICAL FIELD

The present invention relates firstly to a sulfonium salt and secondly to a photo-acid generator. More specifically, the present invention relates to a photo-acid generator comprising a specific sulfonium salt that is decomposed by irradiation with an active energy ray, such as light, an electron beam, or an X-ray, to generate an acid.

BACKGROUND ART

A photo-acid generator is a generic name of compounds which are decomposed by irradiation with an active energy ray, such as light, an electron beam, or an X-ray, to generate an acid, and the acid generated through active energy ray irradiation is used as an active species for various reactions, such as polymerization, crosslinking, and a deprotection reaction. Specific examples of such a reaction include polymerization of a cationically polymerizable compound, a crosslinking reaction of such a compound with a phenol resin in the presence of a crosslinking agent as well as an acid-catalyzed deprotection reaction of a polymer prepared by introducing a protective group to an alkali-soluble resin.

In recent years, while production of electronic parts and semiconductor element formation are performed actively by making full use of a photolithographic technique, chemically amplified resists using acids which are generated from photo-acid generators are used widely. Mass production of semiconductor elements has been carried out using a KrF excimer laser or an ArF excimer laser as an exposure light source, and shorter wavelength light sources such as an electron beam, an EUV (extreme ultraviolet ray), and an X-ray have also been investigated.

Triphenylsulfonium salts are known to have high light sensitivity to the above-mentioned exposure light sources and are used commonly as photo-acid generators for chemically amplified resists.

However, since triphenylsulfonium salts are high in crystallinity because of their symmetrical cation structures, they exhibit low solubility in solvents such as propylene glycol monomethyl ether acetate (PGMEA) and ethyl lactate, for example. Accordingly, they have practical problems, such as a limited amount of addition and incapability of being dispersed uniformly in a composition.

In order to increase the solubility in a solvent, there have been proposed a triphenylsulfonium salt in which the para position of the phenyl ring has been substituted with a fluorine atom, a fluorine-substituted alkyl group, or the like (Patent Document 1, 2) and a triphenylsulfonium salt in which the para position of the phenyl ring has been substituted with an alkyl group (Patent Document 3). However, it is known among those skilled in the art that if a substituent is introduced to the para position of a triphenylsulfonium salt, the light sensitivity is lowered as compared with the unsubstituted salt although the solubility in a solvent is increased.

Although a triphenylsulfonium salt in which the meta position of the phenyl ring has been substituted with an alkyl group (Patent Document 4) has been proposed, the research done by the present inventor has shown that the introduction of an alkyl group to the meta position of a triphenylsulfonium salt lowers the light sensitivity as compared with the unsubstituted salt although the solubility in a solvent is increased.

PRIOR ART DOCUMENTS

Patent Documents

Patent Document 1: WO 2002/018332
Patent Document 2: JP 2005-091976 A
Patent Document 3: JP 2002-193925 A
Patent Document 4: WO 2005/037778

SUMMARY OF THE INVENTION

Problems to be Solved by the Invention

Under the above-mentioned background, a first object of the present invention is to provide a novel sulfonium salt that has high solubility in a solvent and has high light sensitivity to, especially, light having a wavelength not longer than deep-UV (254 nm).

A second object of the present invention is to provide a novel photo-acid generator comprising the above-mentioned sulfonium salt.

Means for Solving the Problems

The present inventor synthesized a sulfonium salt represented by the following formula (1) and found that it is suitable for the above-mentioned objects.

That is, the present invention is a sulfonium salt represented by the following general formula (1):

[Chemical Formula 1]

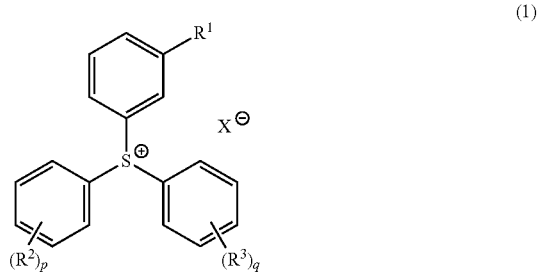

wherein $R^1$ represents an electron withdrawing group; $R^2$ and $R^3$ each independently represent an alkyl group having 1 to 5 carbon atoms, an alkoxy group, an acyl group, a halogenated alkyl group, a halogen atom, a hydroxyl group, a cyano group, or a nitro group; p and q each independently represent an integer of 0 to 5; and $X^-$ represents a monovalent counter anion.

Moreover, the present invention is also a photo-acid generator comprising the above-mentioned sulfonium salt.

Effects of the Invention

The sulfonium salt of the present invention has high solubility in a solvent and excels in light sensitivity to active energy rays, such as deep-UV, a KrF excimer laser, an ArF excimer laser, an electron beam, an EUV (extreme ultraviolet ray), and an X-ray.

The photo-acid generator of the present invention exhibits high solubility in a monomer, a resin, or an organic solvent when being added to an energy ray-curable composition or a chemically amplified resist composition, and therefore it does not deposit after being incorporated and exhibits high dispersibility in a resin, so that it can be added in a larger amount than conventional ones. Moreover, the photo-acid generator excels in light sensitivity by the action of deep-UV, a KrF excimer laser, an ArF excimer laser, an electron beam, an EUV (extreme ultraviolet ray), an X-ray, and the like, so that it can perform a reaction (polymerization, crosslinking, deprotection, or the like) at a lower light exposure amount than conventional ones.

MODE FOR CARRYING OUT THE INVENTION

Embodiments of the present invention are described in detail below.

The sulfonium salt of the present invention is represented by the following general formula (1):

[Chemical Formula 2]

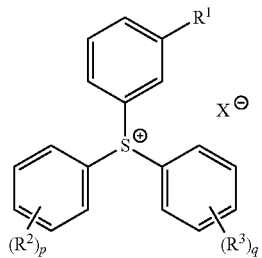

wherein $R^1$ represents an electron withdrawing group; $R^2$ and $R^3$ each independently represent an alkyl group having 1 to 5 carbon atoms, an alkoxy group, an acyl group, a halogenated alkyl group, a halogen atom, a hydroxyl group, a cyano group, or a nitro group; p and q each independently represent an integer of 0 to 5; and $X^-$ represents a monovalent counter anion.

In the general formula (1), the electron withdrawing group as $R^1$ represents in the present invention a substituent whose Hammett's substituent constant $\sigma_m$ is a positive value. The Hammett's $\sigma_m$ value is described in detail in, for example, a review written by Yuho TSUNO (Synthetic Organic Chemistry, Vol. 23, No. 8 (1965) pp. 631-642), "Cram, Organic Chemistry [II], 4th edition" p. 656 translated by Yasuhide YUKAWA (Hirokawa-Shoten Ltd.). Although the electron withdrawing group is prescribed with the $\sigma_m$ value in the present invention, it is not restricted only to the substituents having known values described in the above-mentioned document.

Examples of the electron withdrawing group whose $\sigma_m$ value is positive include alkoxy groups {e.g., a methoxy group ($\sigma_m$ value: 0.12)}, a hydroxyl group (0.12), halogen atoms {e.g., a fluorine atom (0.34), a chlorine atom (0.37), a bromine atom (0.39), and an iodine atom (0.35)}, halogenated alkyl groups {e.g., a trifluoromethyl group (0.43)}, acyloxy groups {e.g., an acetoxy group (0.37)}, acyl groups {e.g., an acetyl group (0.38)}, a cyano group (0.56), a nitro group (0.71), and sulfonyl groups {e.g., a methylsulfonyl group (0.60)}.

Examples of the alkoxy group as the above-mentioned electron withdrawing group and $R^2$ and $R^3$ in the general formula (1) include methoxy, ethoxy, n-propoxy, iso-propoxy, n-butoxy, sec-butoxy, tert-butoxy, n-pentoxy, iso-pentoxy, neo-pentoxy, 2-methylbutoxy, and the like.

Examples of the acyl group include acetyl, ethanoyl, propanoyl, butanoyl, pivaloyl, benzoyl, and the like.

Examples of the halogenated alkyl group include a perfluoroalkyl group in which some or all of the hydrogen atoms in an alkyl group have been substituted with fluorine atoms, and examples of the alkyl group include linear alkyl groups (methyl, ethyl, propyl, butyl, pentyl, octyl, and the like), branched alkyl groups (isopropyl, isobutyl, sec-butyl, tert-butyl, and the like), cycloalkyl groups (cyclopropyl, cyclobutyl, cyclopentyl, cyclohexyl, and the like), and the like.

Examples of the halogen atom include a fluorine atom, a chlorine atom, a bromine atom, an iodine atom, and the like.

Examples of the acyloxy group as the electron withdrawing group include acetoxy, butanoyloxy, benzoyloxy, and the like.

Examples of the sulfonyl group include methanesulfonyl, benzenesulfonyl, toluenesulfonyl, trifluoromethanesulfonyl, difluoromethanesulfonyl, and the like.

Examples of the alkyl group having 1 to 5 carbon atoms as $R^2$ and $R^3$ in the general formula (1) include linear alkyl groups (methyl, ethyl, n-propyl, n-butyl, n-pentyl, and the like), branched alkyl groups (isopropyl, isobutyl, sec-butyl, tert-butyl, isopentyl, neopentyl, tert-pentyl, and the like), cycloalkyl groups (cyclopropyl, cyclobutyl, cyclopentyl, and the like), and the like.

$R^1$, $R^2$, and $R^3$ in the general formula (1) are independent from one another and therefore may be either the same or different from one another.

Among the options of $R^1$, preferred are a perfluoroalkyl group having 1 to 4 carbon atoms, a nitro group, a hydroxyl group, a cyano group, an acyl group having 1 to 4 carbon atoms, and a halogen atom, more preferred are a perfluoroalkyl group having 1 to 4 carbon atoms and a halogen atom, and particularly preferred are a trifluoromethyl group and a fluorine atom. If $R^1$ is within such a preferable range, the light sensitivity and the solubility of the sulfonium salt will be satisfactory.

In the general formula (1), p and q represent the numbers of $R^2$ and $R^3$, respectively and are each an integer of 0 to 5, preferably 0 to 2, more preferably 0 or 1, and most preferably 0. If p and q are within such preferable ranges, the light sensitivity and the solubility of the sulfonium salt will be satisfactory.

Among the sulfonium salts represented by the general formula (1), preferable specific examples are provided below.

[Chemical Formula 3]

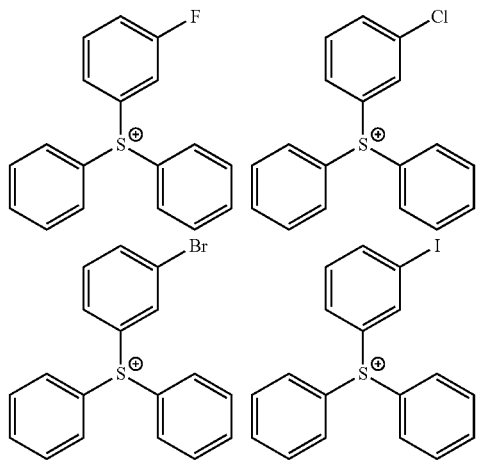

-continued

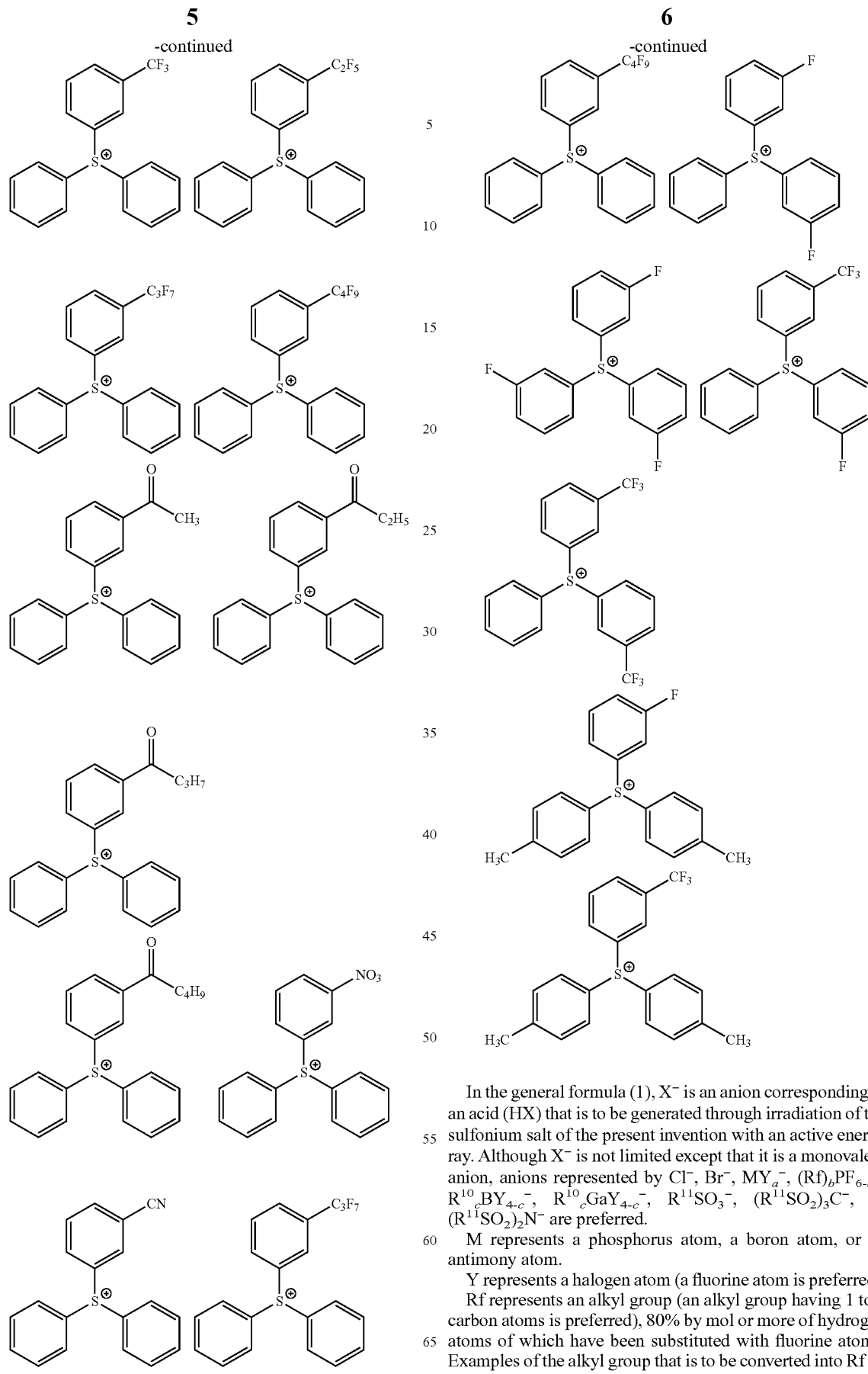

In the general formula (1), X⁻ is an anion corresponding to an acid (HX) that is to be generated through irradiation of the sulfonium salt of the present invention with an active energy ray. Although X⁻ is not limited except that it is a monovalent anion, anions represented by Cl⁻, Br⁻, $MY_a^-$, $(Rf)_bPF_{6-b}^-$, $R^{10}{}_cBY_{4-c}^-$, $R^{10}{}_cGaY_{4-c}^-$, $R^{11}SO_3^-$, $(R^{11}SO_2)_3C^-$, or $(R^{11}SO_2)_2N^-$ are preferred.

M represents a phosphorus atom, a boron atom, or an antimony atom.

Y represents a halogen atom (a fluorine atom is preferred).

Rf represents an alkyl group (an alkyl group having 1 to 8 carbon atoms is preferred), 80% by mol or more of hydrogen atoms of which have been substituted with fluorine atoms. Examples of the alkyl group that is to be converted into Rf by substitution with fluorine include linear alkyl groups (methyl, ethyl, propyl, butyl, pentyl, octyl, and the like), branched alkyl groups (isopropyl, isobutyl, sec-butyl, tert-butyl, and the like), cycloalkyl groups (cyclopropyl, cyclobutyl, cyclopentyl, cyclohexyl, and the like), and the like. The percentage of substitution of the hydrogen atoms of such an alkyl group in Rf with fluorine atoms is preferably 80% by mol or more, more preferably 90% by mol or more, and particularly preferably 100% by mol based on the number of moles of the hydrogen atoms which the alkyl group originally had. If the percentage substituted by fluorine atoms is within such a preferable range, the light sensitivity of the sulfonium salt is further improved. Examples of particularly preferable Rf include $CF_3—$, $CF_3CF_2—$, $(CF_3)_2CF—$, $CF_3CF_2CF_2—$, $CF_3CF_2CF_2CF_2—$, $(CF_3)_2CFCF_2—$, $CF_3CF_2(CF_3)CF—$, and $(CF_3)_3C—$. Rfs, the number of which is b, are independent from one another and therefore may be either the same or different from one another.

P represents a phosphorus atom and F represents a fluorine atom.

$R^{10}$ represents a phenyl group, some of the hydrogen atoms of which have been substituted with at least one element or electron withdrawing group. Examples of such one element include a halogen atom, such as a fluorine atom, a chlorine atom, and a bromine atom. Examples of the electron withdrawing group include a trifluoromethyl group, a nitro group, a cyano group, and the like. Among these, a phenyl group one hydrogen atom of which has been substituted with a fluorine atom or a trifluoromethyl group is preferred. $R^{10}$s, the number of which is c, are independent from one another and therefore may be either the same or different from one another.

B represents a boron atom and Ga represents a gallium atom.

$R^{11}$ represents an alkyl group having 1 to 20 carbon atoms, a perfluoroalkyl group having 1 to 20 carbon atoms, or an aryl group having 6 to 20 carbon atoms, and the alkyl group and the perfluoroalkyl group may be any of linear, branched, and cyclic, and the aryl group may either be unsubstituted or have a substituent.

S represents a sulfur atom, O represents an oxygen atom, C represents a carbon atom, and N represents a nitrogen atom.

a represents an integer of 4 to 6.

b is preferably an integer of 1 to 5, more preferably 2 to 4, and particularly preferably 2 or 3.

c is preferably an integer of 1 to 4, more preferably 4.

Examples of the anion represented by $MY_a^-$ include anions represented by $SbF_6^-$, $PF_6^-$, or $BF_4^-$, and the like.

Examples of the anion represented by $(Rf)_bPF_{6-b}^-$ include anions represented by $(CF_3CF_2)_2PF_4^-$, $(CF_3CF_2)_3PF_3^-$, $((CF_3)_2CF)_2PF_4^-$, $((CF_3)_2CF)_3PF_3^-$, $(CF_3CF_2CF_2)_2PF_4^-$, $(CF_3CF_2CF_2)_3PF_3^-$, $((CF_3)_2CFCF_2)_2PF_4^-$, $((CF_3)_2CFCF_2)_3PF_3^-$, $(CF_3CF_2CF_2CF_2)_2PF_4^-$, or $(CF_3CF_2CF_2CF_2)_3PF_3^-$, and the like.

Examples of the anion represented by $R^{10}_cBY_{4-c}^-$ include anions represented by $(C_6F_5)_4B^-$, $((CF_3)_2C_6H_3)_4B^-$, $(CF_3C_6H_4)_4B^-$, $(C_6F_5)_2BF_2^-$, $C_6F_5BF_3^-$, or $(C_6H_3F_2)_4B^-$, and the like.

Examples of the anion represented by $R^{10}_cGaY_{4-c}^-$ include anions represented by $(C_6F_5)_4Ga^-$, $((CF_3)_2C_6H_3)_4Ga^-$, $(CF_3C_6H_4)_4Ga^-$, $(C_6F_5)_2GaF_2^-$, $C_6F_5GaF_3^-$, or $(C_6H_3F_2)_4Ga^-$, and the like.

Examples of the anion represented by $R^{11}SO_3^-$ include a trifluoromethanesulfonate anion, a pentafluoroethanesulfonate anion, a heptafluoropropanesulfonate anion, a nonafluorobutanesulfonate anion, a pentafluorophenylsulfonate anion, a p-toluenesulfonate anion, a benzenesulfonate anion, a camphorsulfonate anion, a methanesulfonate anion, an ethanesulfonate anion, a propanesulfonate anion, a butanesulfonate anion, and the like.

Examples of the anion represented by $(R^{11}SO_2)_3C^-$ include anions represented by $(CF_3SO_2)_3C^-$, $(C_2F_5SO_2)_3C^-$, $(C_3F_7SO_2)_3C^-$, or $(C_4F_9SO_2)_3C^-$, and the like.

Examples of the anion represented by $(R^{11}SO_2)_2N^-$ include anions represented by $(CF_3SO_2)_2N^-$, $(C_2F_5SO_2)_2N^-$, $(C_3F_7SO_2)_2N^-$, or $(C_4F_9SO_2)_2N^-$, and the like.

Examples of anions that can be used as a monovalent polyatomic anion include perhalate ions ($ClO_4^-$, $BrO_4^-$, and the like), halogenated sulfonate ions ($FSO_3^-$, $ClSO_3^-$, and the like), sulfate ions ($CH_3SO_4^-$, $CF_3SO_4^-$, $HSO_4^-$, and the like), carbonate ions ($HCO_3^-$, $CH_3CO_3^-$, and the like), aluminate ions ($AlCl_4^-$, $AlF_4^-$, and the like), a hexafluorobismuthate ion ($BiF_6^-$), carboxylate ions ($CH_3COO^-$, $CF_3COO^-$, $C_6H_5COO^-$, $CH_3C_6H_4COO^-$, $C_6F_5COO^-$, $CF_3C_6H_4COO^-$, and the like), arylborate ions $\{B(C_6H_5)_4^-$, $CH_3CH_2CH_2CH_2B(C_6H_5)_3^-$, and the like$\}$, a thiocyanate ion ($SCN^-$), a nitrate ion ($NO_3^-$), and the like in addition to anions represented by $MY_a^-$, $(Rf)_bPF_{6-b}^-$, $R^{10}_cBY_{4-c}^-$, $R^{10}_cGaY_{4-c}^-$, $R^{11}SO_3^-$, $(R^{11}SO_2)_3C^-$, or $(R^{11}SO_2)_2N^-$.

Examples of anions other than the above include anions described in JP 2013-092657 A, JP 2013-080245 A, JP 2013-080240 A, JP 2013-047211 A, JP 2013-033161 A, and the like.

Among the options of $X^-$, preferred are $Cl^-$, $Br^-$, $SbF_6^-$, $PF_6^-$, $BF_4^-$, $(CF_3CF_2)_3PF_3^-$, $(CF_3CF_2)_2PF_4^-$, $(CF_3CF_2)PF_5^-$, $(C_6F_5)_4B^-$, $\{(CF_3)_2C_6H_3\}_4B^-$, $(C_6F_5)_4Ga^-$, $\{(CF_3)_2C_6H_3\}_4Ga^-$, a trifluoromethanesulfonate anion, a nonafluorobutanesulfonate anion, a methanesulfonate anion, a butanesulfonate anion, a camphorsulfonate anion, a benzenesulfonate anion, a p-toluenesulfonate anion, and anions represented by $(CF_3SO_2)_3C^-$, $(CF_3SO_2)_2N^-$, or $(C_4F_9SO_2)_2N^-$.

The sulfonium salt can be produced by the production method described below.

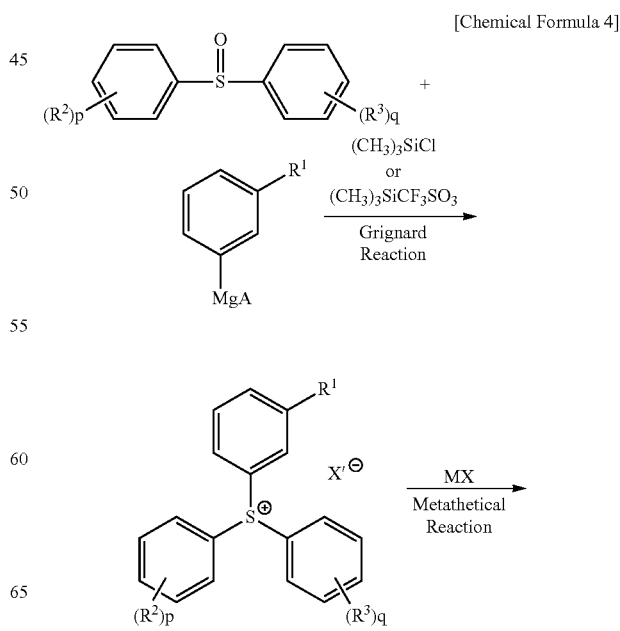

[Chemical Formula 4]

-continued

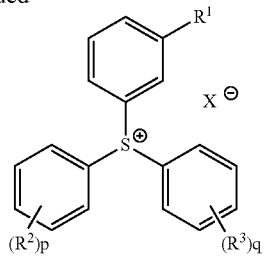

In the above-mentioned reaction formula, A represents a halogen atom, $X'^-$ represents $Cl^-$ or a trifluoromethanesulfonate anion, and MX represents a salt of an alkali metal (lithium, sodium, potassium, or the like) cation with another monovalent anion of the present invention.

$R^1$, $R^2$, $R^3$, p, q, and $X^-$ are as defined in the general formula (1).

$X'^-$ can be replaced with another anion ($X^-$) of the present invention by, for example, a metathetical reaction as described above.

In the above-mentioned reaction formula, the reaction of the first stage may be performed in the absence of a solvent or alternatively may be performed in an organic solvent (a common solvent to be used for a Grignard reaction such as tetrahydrofuran, chloroform, or dichloromethane) as necessary. The reaction temperature is about −20 to about 150° C. while depending upon the boiling point of the solvent to be used. The reaction time is about 1 to about several tens of hours.

The reaction of the second stage may be performed subsequent to the reaction of the first stage or alternatively may be performed after isolating (as necessary, purifying) a precursor. The sulfonium salt of the present invention is obtained in the form of a solid or a viscous liquid by mixing and stirring the precursor with an aqueous solution of a salt (MX) of an alkali metal cation with a monovalent anion to perform a metathetical reaction, and then collecting a solid that deposits or extracting a discrete oily matter with an organic solvent, followed by removal of the organic solvent. The resulting solid or viscous liquid may be washed with a proper organic solvent or purified by a recrystallization method or column chromatography as necessary.

The chemical structure of the sulfonium salt of the present invention can be identified by a common analytical technique (e.g., $^1H-$, $^{11}B-$, $^{13}C-$, $^{19}F-$, $^{31}P$-nuclear magnetic resonance spectrum, infrared absorption spectrum and/or elemental analysis, or the like).

While the photo-acid generator of the present invention comprises a sulfonium salt represented by the formula (1), it may be used with a different conventional photo-acid generator comprised in addition to the photo-acid generator represented by the formula (1).

When a different photo-acid generator is contained, the content (% by mol) of the different photo-acid generator is preferably 0.1 to 100, and more preferably 0.5 to 50 relative to the overall number of moles of the sulfonium salt represented by the formula (1) of the present invention.

Examples of the different photo-acid generator include conventionally known ones such as onium salts (sulfonium, iodonium, selenium, ammonium, phosphonium, and the like) and salts of a transition metal complex ion with an anion.

When using a sulfonium salt (photo-acid generator) represented by the formula (1), it may be beforehand dissolved in a solvent that does not inhibit polymerization, crosslinking, a deprotection reaction, and the like in order to make easier its dissolution in a cationically polymerizable compound or a chemically amplified resist composition.

Examples of the solvent include carbonates such as propylene carbonate, ethylene carbonate, 1,2-butylene carbonate, dimethyl carbonate, and diethyl carbonate; ketones such as acetone, methyl ethyl ketone, cyclopentanone, cyclohexanone, methyl isoamyl ketone, and 2-heptanone; polyhydric alcohols and derivatives thereof such as ethylene glycol, ethylene glycol monoacetate, diethylene glycol, diethylene glycol monoacetate, propylene glycol, propylene glycol monoacetate, dipropylene glycol, and monomethyl ether, monoethyl ether, monopropyl ether, monobutyl ether, or monophenyl ether of dipropylene glycol monoacetate; cyclic ethers such as dioxane; esters such as ethyl formate, methyl lactate, ethyl lactate, methyl acetate, ethyl acetate, butyl acetate, methyl pyruvate, methyl acetoacetate, ethyl acetoacetate, ethyl pyruvate, ethoxyethyl acetate, methoxymethyl propionate, ethoxyethyl propionate, methyl 2-hydroxypropionate, ethyl 2-hydroxypropionate, ethyl 2-hydroxy-2-methylpropionate, methyl 2-hydroxy-3-methylbutanoate, 3-methoxybutyl acetate, and 3-methyl-3-methoxybutyl acetate; and aromatic hydrocarbons such as toluene and xylene.

When a solvent is used, the solvent is used in a proportion of preferably 15 to 1000 parts by weight, and more preferably 30 to 500 parts by weight per 100 parts by weight of the sulfonium salt (photo-acid generator) represented by the formula (1) of the present invention. Solvents to be used may be used individually or alternatively two or more solvents may be used in combination.

EXAMPLES

The present invention is further described by way of examples below, but the invention is not intended to be limited thereto. Unless otherwise stated, % means % by weight.

Example 1

Synthesis of Photo-Acid Generator (A-1)

(1) Synthesis of 3-fluorophenylmagnesium bromide

A reactor that had been degassed and purged with nitrogen was charged with 28.0 parts of magnesium and 62.0 parts of tetrahydrofuran, and 173 parts of 3-bromofluorobenzene and 330 parts of tetrahydrofuran were fed into a dropping funnel and then dropped so that the internal temperature might not exceed 60° C. After the completion of the dropping, a reaction was continued at 40 to 60° C. for 1 hour and then 710 parts of tetrahydrofuran was fed, affording a tetrahydrofuran solution of 3-fluorophenylmagnesium bromide.

(2) Synthesis of a Target Product

A reactor that had been degassed and purged with nitrogen was charged with 66.3 parts of diphenyl sulfoxide, 652 parts of tetrahydrofuran, and 510 parts of trimethylsilyl trifluoromethanesulfonate and then cooled to 5° C. in an ice bath. Subsequently, the tetrahydrofuran solution of 3-fluorophenylmagnesium bromide synthesized in (1) was cooled to 5° C. in an ice bath and then it was dropped from a dropping funnel so that the internal temperature might not exceed 15° C. After the completion of the dropping, a reaction was continued at 10° C. for 1 hour and then the reaction was completed.

The resulting solution was added to 3400 parts of ion-exchanged water cooled to 5° C. in an ice bath so that the temperature might not exceed 15° C., and after the completion of the addition, stirring was carried out for 1 hour so that the temperature might not exceed 25° C. Subsequently, 3200 parts of toluene was fed, followed by stirring for 1 hour. A toluene layer was then removed and the remaining solution was washed twice with 1600 parts of toluene. Then, the solution was extracted by addition of 3200 parts of dichloromethane and then the water layer was separated away. Moreover, the organic layer was washed four times with 1200 parts of ion-exchanged water. The organic layer was desolvated, and 75.0 parts of dichloromethane was added to the resulting yellow oily residue to dissolve the residue. The resulting solution was charged slowly into 1500 parts of diethyl ether under stirring and thereby a pale yellow solid was deposited. This solid was collected by filtration and then was dissolved by addition of 480 parts of dichloromethane. To the resulting solution was fed 650 parts of diethyl ether slowly under stirring and thereby white needle crystals were deposited. The crystals were collected by filtration and then dried under reduced pressure, affording 114.0 parts of a target photo-acid generator (A-1) in a yield of 81% (purity: 99.8% or more). The product was identified by $^1$H-NMR and $^{19}$F-NMR {$^1$H-NMR, d$_6$-dimethyl sulfoxide, δ (ppm): 7.95-7.70 (13H, m), 7.60 (1H, d)}. {$^{19}$F-NMR, d$_6$-dimethyl sulfoxide, δ (ppm): −74 (3F, s), −104 (1F, s); internal standard substance=hexafluorobenzene, −159 (6F, s)}. The structure of A-1 is shown in Table 1.

Example 2

Synthesis of Photo-Acid Generator (A-2)

In 180 parts of dichloromethane was dissolved 20.0 parts of (A-1) synthesized in Example 1, and then the resulting solution was added to 1260 parts of a 5% aqueous solution of potassium nonafluorobutanesulfonate, followed by stirring at 25° C. for 2 hours. After the water layer was removed, 1260 parts of a 5% aqueous solution of potassium nonafluorobutanesulfonate was added to the organic layer, followed by stirring again at 25° C. for 2 hours. After the water layer was removed, the organic layer was washed several times with water and then dried under reduced pressure, affording 23.2 parts of a target photo-acid generator (A-2) in a yield of 86%. The product was identified by $^{19}$F-NMR {$^{19}$F-NMR, d$_6$-dimethyl sulfoxide, δ (ppm): −77 (3F, s), −104 (1F, s), −111 (2F, t), −118 (2F, s), −122 (2F, t); internal standard substance=hexafluorobenzene, −159 (6F, s)}. The structure of A-2 is shown in Table 1.

Example 3

Synthesis of Photo-Acid Generator (A-3)

In 180 parts of dichloromethane was dissolved 20.0 parts of (A-1) synthesized in Example 1, and then the resulting solution was added to 157 parts of a 10% aqueous solution of bis(nonafluorobutanesulfonyl)imide, followed by stirring at 25° C. for 3 hours. The organic layer was washed several times with water and then dried under reduced pressure, affording 24.0 parts of a target photo-acid generator (A-3) in a yield of 92%. The product was identified by $^{19}$F-NMR {$^{19}$F-NMR, d$_6$-dimethyl sulfoxide, δ (ppm): −77 (6F, t), −104 (1F, s), −110 (4F, t), −117 (4F, s), −122 (4F, t); internal standard substance=hexafluorobenzene, −159 (6F, s)}. The structure of A-3 is shown in Table 1.

Example 4

Synthesis of Photo-Acid Generator (A-4)

In 180 parts of dichloromethane was dissolved 20.0 parts of (A-1) synthesized in Example 1, and then the resulting solution was added to 211 parts of a 10% aqueous solution of tris(trifluoromethanesulfonyl)methide, followed by stirring at 25° C. for 3 hours. The organic layer was washed several times with water and then dried under reduced pressure, affording 29.0 parts of a target photo-acid generator (A-4) in a yield of 90%. The product was identified by $^{19}$F-NMR {$^{19}$F-NMR, d$_6$-dimethyl sulfoxide, δ (ppm): −73 (9F, s), −104 (1F, s); internal standard substance=hexafluorobenzene, −159 (6F, s)}. The structure of A-4 is shown in Table 1.

Example 5

Synthesis of Photo-Acid Generator (A-5)

A target photo-acid generator (A-5) was obtained similarly to Example 2. The product was identified by $^1$H-NMR {$^1$H-NMR, d$_6$-dimethyl sulfoxide, δ (ppm): 7.50-8.00 (14H, m, ArH), 2.88 (1H, d, CH), 2.66-2.74 (1H, m, CH), 2.37 (1H, d, CH), 2.17-2.24 (1H, m, CH), 1.90 (1H, t, CH), 1.74-1.89 (2H, m, CH$_2$), 1.22-1.29 (2H, m, CH$_2$), 1.03 (3H, s, CH$_3$), 0.71 (3H, s, CH$_3$)}. The structure of A-5 is shown in Table 1.

Example 6

Synthesis of Photo-Acid Generator (A-6)

(1) Synthesis of 3-trifluoromethylphenylmagnesium bromide

A reactor that had been degassed and purged with nitrogen was charged with 19.0 parts of magnesium and 45.0 parts of tetrahydrofuran, and 150 parts of 3-bromobenzotrifluoride and 222 parts of tetrahydrofuran were fed into a dropping funnel and then dropped so that the internal temperature might not exceed 60° C. After the completion of the dropping, a reaction was continued at 40 to 60° C. for 1 hour and then 477 parts of tetrahydrofuran was fed, affording a tetrahydrofuran solution of 3-trifluoromethylphenylmagnesium bromide.

(2) Synthesis of a Target Product

A reactor that had been degassed and purged with nitrogen was charged with 45.0 parts of diphenyl sulfoxide, 444 parts of tetrahydrofuran, and 345 parts of trimethylsilyl trifluoromethanesulfonate and then cooled to 5° C. in an ice bath. Subsequently, the tetrahydrofuran solution of 3-trifluoromethylphenylmagnesium bromide synthesized in (1) was cooled to 5° C. in an ice bath and then it was dropped from a dropping funnel so that the internal temperature might not exceed 15° C. After the completion of the dropping, a reaction was continued at 10° C. for 1 hour and then the reaction was completed.

The resulting solution was added to 2400 parts of ion-exchanged water cooled to 5° C. in an ice bath so that the temperature might not exceed 15° C., and after the completion of the addition, stirring was carried out for 1 hour so that the temperature might not exceed 25° C. Subsequently, 2300 parts of toluene was fed, followed by stirring for 1 hour. A toluene layer was then removed and the remaining solution was washed twice with 1150 parts of toluene. Then, the solution was extracted by addition of 2300 parts of dichloromethane and then the water layer was separated away. Moreover, the organic layer was washed four times with 850 parts of ion-exchanged water. The organic layer was desolvated, and 55.0 parts of dichloromethane was added to the resulting yellow oily residue to dissolve the residue. The resulting solution was charged slowly into 1050 parts of diethyl ether under stirring and thereby a pale yellow solid was deposited. This solid was collected by filtration and then was dissolved by addition of 350 parts of dichloromethane.

To the resulting solution was fed 450 parts of diethyl ether slowly under stirring and thereby white needle crystals were deposited. The crystals were collected by filtration and dried under reduced pressure, affording 75.0 parts of a target product, diphenyl-3-trifluoromethylphenylsulfonium trifluoromethane sulfonate in a yield of 70% (purity: 99.9% or more). The product was identified by $^1$H-NMR and $^{19}$F-NMR {$^1$H-NMR, $d_6$-dimethyl sulfoxide, δ (ppm): 8.40 (1H, s), 8.20 (1H, d), 8.05-7.70 (12H, m)}. {$^{19}$F-NMR, $d_6$-dimethyl sulfoxide, δ (ppm): −58 (3F, s), −74 (3F, s); internal standard substance=hexafluorobenzene, −159 (6F, s)}. The structure of A-6 is shown in Table 1.

Example 7

Synthesis of Photo-Acid Generator (A-7)

In 180 parts of dichloromethane was dissolved 20.0 parts of (A-6) synthesized in Example 6, and then the resulting solution was added to 1130 parts of a 5% aqueous solution of potassium nonafluorobutanesulfonate, followed by stirring at 25° C. for 2 hours. After the water layer was removed, 1130 parts of a 5% aqueous solution of potassium nonafluorobutanesulfonate was added to the organic layer, followed by stirring again at 25° C. for 2 hours. After the water layer was removed, the organic layer was washed several times with water and then dried under reduced pressure, affording 21.3 parts of a target photo-acid generator (A-7) in a yield of 81%. The product was identified by $^{19}$F-NMR {$^{19}$F-NMR, $d_6$-dimethyl sulfoxide, δ (ppm): −58 (3F, s), −77 (3F, t), −111 (2F, t), −118 (2F, s), −122 (2F, t); internal standard substance=hexafluorobenzene, −159 (6F, s)}. The structure of A-7 is shown in Table 1.

Example 8

Synthesis of Photo-Acid Generator (A-8)

In 180 parts of dichloromethane was dissolved 20.0 parts of (A-6) synthesized in Example 6, and then the resulting solution was added to 140 parts of a 10% aqueous solution of bis(nonafluorobutanesulfonyl)imide, followed by stirring at 25° C. for 3 hours. The organic layer was washed several times with water and then dried under reduced pressure, affording 22.4 parts of a target photo-acid generator (A-8) in a yield of 88%. The product was identified by $^{19}$F-NMR {$^{19}$F-NMR, $d_6$-dimethyl sulfoxide, δ (ppm): −58 (3F, s), −77 (6F, t), −110 (4F, t), −117 (4F, s), −122 (4F, t); internal standard substance=hexafluorobenzene, −159 (6F, s)}. The structure of A-8 is shown in Table 1.

Example 9

Synthesis of Photo-Acid Generator (A-9)

In 180 parts of dichloromethane was dissolved 20.0 parts of (A-6) synthesized in Example 6, and then the resulting solution was added to 189 parts of a 10% aqueous solution of tris(trifluoromethanesulfonyl)methide, followed by stirring at 25° C. for 3 hours. The organic layer was washed several times with water and then dried under reduced pressure, affording 26.3 parts of a target photo-acid generator (A-9) in a yield of 85%. The product was identified by $^{19}$F-NMR {$^{19}$F-NMR, $d_6$-dimethyl sulfoxide, δ (ppm): −58 (3F, s), −73 (9F, s); internal standard substance=hexafluorobenzene, −159 (6F, s)}. The structure of A-9 is shown in Table 1.

Example 10

Synthesis of Photo-Acid Generator (A-10)

A target photo-acid generator (A-10) was obtained similarly to Example 6. The product was identified by $^1$H-NMR {$^1$H-NMR, $d_6$-dimethyl sulfoxide, δ (ppm): 7.74-7.90 (12H, m, ArH), 8.25 (1H, d, ArH), 8.50 (1H, s, ArH), 2.88 (1H, d, CH), 2.66-2.74 (1H, m, CH), 2.37 (1H, d, CH), 2.17-2.24 (1H, m, CH), 1.90 (1H, t, CH), 1.74-1.89 (2H, m, $CH_2$), 1.22-1.29 (2H, m, $CH_2$), 1.03 (3H, s, $CH_3$), 0.71 (3H, s, $CH_3$)}. The structure of A-10 is shown in Table 1.

TABLE 1

| | Cation | Anion |
|---|---|---|
| A-1 | | $CF_3SO_3^{\ominus}$ |
| A-2 | | $C_4F_9SO_3^{\ominus}$ |
| A-3 | | $(C_4F_9SO_2)_2N^{\ominus}$ |
| A-4 | | $(CF_3SO_2)_3C^{\ominus}$ |
| A-5 | (3-fluorophenyl)diphenylsulfonium cation | camphorsulfonate anion |
| A-6 | | $CF_3SO_3^{\ominus}$ |
| A-7 | | $C_4F_9SO_3^{\ominus}$ |
| A-8 | | $(C_4F_9SO_2)_2N^{\ominus}$ |
| A-9 | | $(CF_3SO_2)_3C^{\ominus}$ |
| A-10 | (3-trifluoromethylphenyl)diphenylsulfonium cation | camphorsulfonate anion |

Comparative Example 1

Triphenylsulfonium trifluoromethanesulfonate (produced by Sigma-Aldrich) was designated as a comparative photo-acid generator (H-1).

Comparative Example 2

(4-Methylphenyl)diphenylsulfonium trifluoromethanesulfonate (produced by Sigma-Aldrich) was designated as a comparative photo-acid generator (H-2).

Comparative Example 3

(4-Fluorophenyl)diphenylsulfonium trifluoromethanesulfonate (produced by Sigma-Aldrich) was designated as a comparative photo-acid generator (H-3).

<Evaluation of Light Sensitivity>
(Preparation of Sample Solution)

The photo-acid generators (A-1) to (A-10) of the present invention and the photo-acid generators (H-1) to (H-3) of comparative examples were each diluted with acetonitrile so that their molar concentrations would be 2.5 mM, and then Rhodamine B base (a color reagent for an acid, produced by Sigma-Aldrich) was added to the respective solutions so that the molar concentration would be 2.5 mM, yielding sample solutions.

(Measurement of Acid Generation Ratio)

A sample solution obtained above was put into a quartz cell having an optical path length of 1 cm and then was exposed to light under prescribed conditions using an ArF excimer lamp (center wavelength=193 nm). The absorbance near 556 nm of the respective sample solutions after exposure to light was measured with a spectrophotometer (UV-vis) because the photo-acid generator in a sample solution is decomposed upon exposure to light to generate an acid, which then reacts with Rhodamine B base and, as a result, the absorbance near 556 nm increases. Based on the absorbance at 556 nm, the molar concentration of the acid in the sample solution after exposure to light was determined using a calibration curve (standard substance: p-toluenesulfonic acid). From the acid concentration determined and the initial concentration of the photo-acid generator, the acid generation ratio was determined by the following calculation. A higher acid generation ratio indicates superior light sensitivity.

Acid generation ratio (%)=Acid concentration (mM) after exposure to light/Photo-acid generator concentration (mM) before exposure to light×100

(Evaluation)

The acid generation ratio determined by the above-mentioned operations was judged according to the following criteria. The results are shown in Table 2.

A: 55% or more
C: less than 55%

(Light Exposure Conditions)

Photolithography machine: ArF excimer lamp (manufactured by USHIO INC.)
Illuminance (measured with a 193 nm head illuminometer): 1.8 mW/cm$^2$
Integrated amount of light (measured with a 193 nm head illuminometer): 100 mJ/cm$^2$ <Evaluation of Solubility>

(Measurement of Degree of Solubility)

The degrees of solubility in propylene glycol monomethyl ether acetate (PGMEA) of the photo-acid generators (A-1) to (A-10) of the present invention and the photo-acid generators (H-1) to (H-3) of comparative examples were measured. A higher degree of solubility indicates superior solubility.

(Evaluation)

The degree of solubility determined by the above-mentioned operations was judged according to the following criteria. The results are shown in Table 2.

S: 30% or more
A: 5% or more but less than 30%
B: 1% or more but less than 5%
C: less than 1%

TABLE 2

| | Photo-acid generator | Degree of solubility (%) | Acid generation ratio (%) |
|---|---|---|---|
| Example 1 | A-1 | A | A |
| Example 2 | A-2 | S | A |
| Example 3 | A-3 | S | A |
| Example 4 | A-4 | S | A |
| Example 5 | A-5 | A | A |
| Example 6 | A-6 | A | A |
| Example 7 | A-7 | S | A |
| Example 8 | A-8 | S | A |
| Example 9 | A-9 | S | A |
| Example 10 | A-10 | A | A |
| Comparative Example 1 | H-1 | C | A |
| Comparative Example 2 | H-2 | B | C |
| Comparative Example 3 | H-3 | B | C |

As shown in Table 2, it is shown that when comparing Examples 1 and 6 with Comparative Examples 1 to 3 which are identical in their anion portions and different in their cation portions, Examples 1 and 6 are higher in the degree of solubility in PGMEA than Comparative Examples 1 to 3. When comparing Examples 1 to 10 with Comparative Examples 1 to 3, it is shown that in Examples 1 to 10 were achieved acid generation ratios equal to or higher than those achieved in Comparative Examples 1 to 3.

The above-mentioned results show that the photo-acid generators of the present invention of Examples 1 to 10 are superior to conventional photo-acid generators like those of Comparative Examples 1 to 3 in both solubility and light sensitivity.

Industrial Applicability

The sulfonium salt of the present invention is used suitably as a photo-acid generator to be used for paints, coating agents, various coating materials (hard coat, anti-pollution coating materials, anti-clouding coating materials, touch-resistant coating materials, optical fibers, and the like), backside treating agents for pressure-sensitive adhesive tapes, release coating materials for release sheets for pressure-sensitive adhesive labels (release paper, release plastic films, release metal foils, and the like), printing boards, dental materials (dental compounds and dental composites), inks, inkjet inks, chemically amplified resists for semiconductor integrated circuits (ultraviolet rays, deep-UV, KrF excimer lasers, ArF excimer lasers, electron beams, EUVs, and X-rays), positive-type resists (formation of connecting terminals or wiring patterns in production of electronic parts such as circuit boards, CSP, and MEMS elements, and the like), resist films, liquid-type resists, negative-type resists (permanent film materials for surface protective films, interlayer insulating films, and planarization films of semiconductor elements, and the like), resists for MEMS, positive-type photosensitive materials, negative-type photosensitive materials, various adhesives (temporary fixing agents for various electronic parts, adhesives for HDD, adhesives for pickup lenses, adhesives for functional films for FPD (deflecting plates, antireflection films, and the like), and the like), resins for holographs, FPD materials (color filters, black matrices, partition materials, photo spacers, ribs, orientation films for liquid crystals, sealing agents for FPD, and the like), optical members, molding materials (building materials, optical parts, and lenses), casting materials, putty materials, glass fiber impregnating agents, fillers, sealing materials, sealants, optical semiconductor (LED) sealants, optical waveguide materials, nanoimprint materials, stereolithography materials, micro-stereolithography materials, and the like.

What is claimed is:

1. A sulfonium salt represented by the following general formula (1):

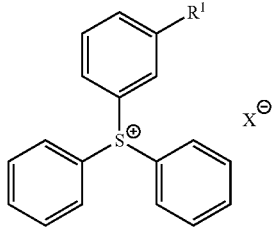

wherein $R^1$ represents an electron withdrawing group; and $X^-$ represents a monovalent counter anion.

2. The sulfonium salt according to claim 1, wherein $R^1$ is a perfluoroalkyl group having 1 to 4 carbon atoms, a nitro group, a hydroxyl group, a cyano group, an acyl group having 1 to 4 carbon atoms, or a halogen atom.

3. The sulfonium salt according to claim 1, wherein $R^1$ is a perfluoroalkyl group having 1 to 4 carbon atoms or a halogen atom.

4. The sulfonium salt according to claim 1, wherein $R^1$ is a trifluoromethyl group or a fluorine atom.

5. The sulfonium salt according to claim 1, wherein $X^-$ is an anion selected from the group consisting of $Cl^-$, $Br^-$, $SbF_6^-$, $PF_6^-$, $BF_4^-$, $(CF_3CF_2)_3PF_3^-$, $(CF_3CF_2)_2PF_4^-$, $(CF_3CF_2)PF_5^-$, $(C_6F_5)_4B^-$, $\{(CF_3)_2C_6H_3\}_4B^-$, $(C_6F_5)_4Ga^-$, $\{(CF_3)_2C_6H_3\}_4Ga^-$, a trifluoromethanesulfonate anion, a nonafluorobutanesulfonate anion, a methanesulfonate anion, a butanesulfonate anion, a camphorsulfonate anion, a benzenesulfonate anion, a p-toluenesulfonate anion, $(CF_3SO_2)_3C^-$, $(CF_3SO_2)_2N^-$, and $(C_4F_9SO_2)_2N^-$.

6. A photo-acid generator comprising the sulfonium salt according to claim 1.

* * * * *